(12) United States Patent
Burgoon et al.

(10) Patent No.: US 7,998,994 B2
(45) Date of Patent: Aug. 16, 2011

(54) SOLID FORMS OF (1R,2S,3R)-1-(2-(ISOXAZOL-3-YL)-1H-IMIDAZOL-4-YL)BUTANE-1,2,3,4-TETRAOL AND METHODS OF THEIR USE

(75) Inventors: Hugh Alfred Burgoon, Hamilton, NJ (US); Suzanne Marie Buttar, Cambridge (GB); Christopher Stephen Frampton, Stowmarket (GB)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 57 days.

(21) Appl. No.: 12/485,444

(22) Filed: Jun. 16, 2009

(65) Prior Publication Data

US 2009/0318516 A1  Dec. 24, 2009

Related U.S. Application Data

(60) Provisional application No. 61/073,398, filed on Jun. 18, 2008.

(51) Int. Cl.
*A61K 31/422* (2006.01)
*C07D 261/06* (2006.01)

(52) U.S. Cl. ...................................... 514/378; 548/247
(58) Field of Classification Search .................. 548/247; 514/378
See application file for complete search history.

(56) References Cited

U.S. PATENT DOCUMENTS

| 4,567,194 | A | 1/1986 | Kroeplien |
| 7,598,280 | B2 | 10/2009 | Augeri |
| 7,649,098 | B2 | 1/2010 | Augeri |
| 7,825,142 | B2 | 11/2010 | Augeri |
| 2008/0275099 | A1 | 11/2008 | Wu |
| 2009/0318705 | A1 | 12/2009 | Guohua et al. |

FOREIGN PATENT DOCUMENTS

| WO | WO 97/46543 | | 12/1997 |
| WO | WO 2007/002458 | | 1/2007 |
| WO | WO-2010022217 | * | 2/2010 |

OTHER PUBLICATIONS

U.S. Appl. No. 12/903,657, filed Oct. 13, 2010, Augeri.
Bagdanoff, J.T., et al., *J. Med. Chem.* 52:3941-3953 (2009).
Cliff and Pyne, *J. Org. Chem.*, 62: 1023-1032 (1997).
Cliff and Pyne, *Tett. Letters*, 36(33): 5969-5972 (1995).
Pyne and Ung, *Synlett* 280-282 (1998).
Halweg and Buchi, *J. Org. Chem.* 50(7): 1134-6 (1985).
Pyne, *ACGC Chem. Res. Comm.* 11:108-112 (2000).
Schwab, S.R., et al. *Science* 309:1735-1739 (2005).
Sweeny, J.R. et al., *J. Org. Chem.* 50:1133-1134 (1985).
PCT International Search Report and Written Opinion of the International Searching Authority dated Apr. 2, 2010, for International Application No. PCT/US2009/047488, filed Jun. 16, 2009.

* cited by examiner

*Primary Examiner* — Joseph K. McKane
*Assistant Examiner* — Janet L Coppins
(74) *Attorney, Agent, or Firm* — Max Bachrach

(57) ABSTRACT

Solid forms of (1R,2S,3R)-1-(2-(isoxazol-3-yl)-1H-imidazol-4-yl)butane-1,2,3,4-tetraol and hydrates thereof are disclosed, as well as compositions comprising them and methods of their use.

8 Claims, 5 Drawing Sheets

SOLID FORMS OF (1R,2S,3R)-1-(2-(ISOXAZOL-3-YL)-1H-IMIDAZOL-4-YL)BUTANE-1,2,3,4-TETRAOL AND METHODS OF THEIR USE

This application claims priority to U.S. provisional application No. 61/073,398, filed Jun. 18, 2008, the entirety of which is incorporated herein by reference.

1. FIELD OF THE INVENTION

This invention relates to solid forms of (1R,2S,3R)-1-(2-(isoxazol-3-yl)-1H-imidazol-4-yl)butane-1,2,3,4-tetraol.

2. BACKGROUND OF THE INVENTION

Different solid forms of the same compound can have substantially different properties. For example, the amorphous form of a drug may exhibit different dissolution characteristics and different bioavailability patterns than its crystalline form(s), properties which can affect how the drug must be administered to achieve optimal effect. Amorphous and crystalline forms of a drug may also have different handling properties (e.g., flowability, compressibility), dissolution rates, solubilities and stabilities, all of which can affect the manufacture of dosage forms. Consequently, access to multiple forms of a drug is desirable for a variety of reasons. Moreover, regulatory authorities (e.g., the U.S. Food and Drug Administration) may require the identification of all solid (e.g., polymorphic) forms of a new drug substance before products containing it. A. Goho, *Science News* 166(8): 122-123 (2004).

Compounds may exist in one or more crystalline forms, but the existence and characteristics of those forms cannot be predicted with any certainty. In addition, no standard procedure exists for the preparation of all possible polymorphic forms of a compound. And even after one polymorph has been identified, the existence and characteristics of other forms can only be determined by additional experimentation. Id.

3. SUMMARY OF THE INVENTION

This invention is directed, in part, to solid forms of (1R, 2S,3R)-1-(2-(isoxazol-3-yl)-1H-imidazol-4-yl)butane-1,2,3, 4-tetraol and hydrates thereof. Particular solid forms are crystalline.

One embodiment of the invention encompasses pharmaceutical compositions comprising the solid forms described herein.

Another embodiment encompasses methods of treating, managing and preventing various diseases and conditions, which comprise the use of the solid forms described herein.

4. BRIEF DESCRIPTION OF THE FIGURES

Figure 5:
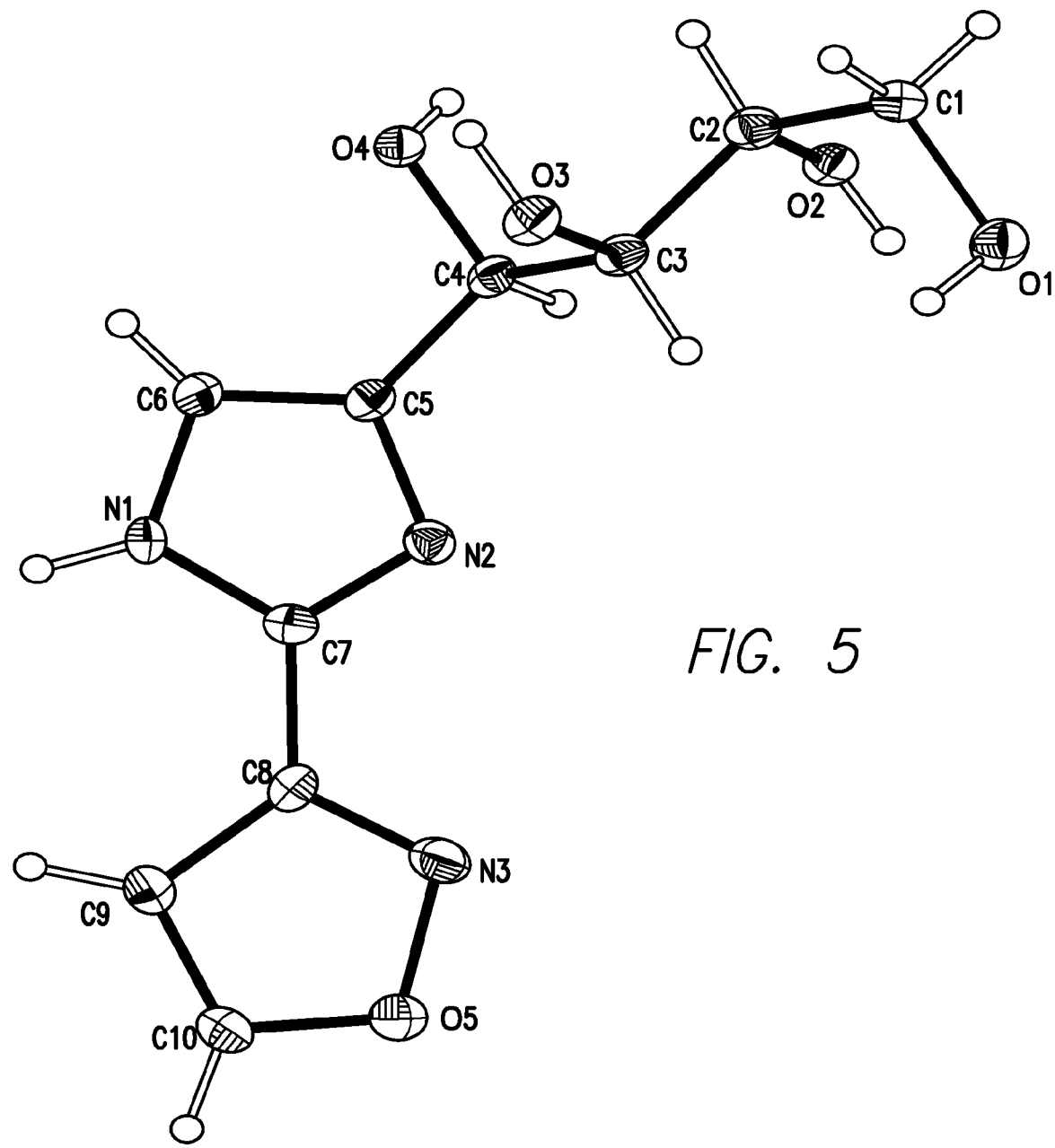

FIG. 5 is a representation of anhydrous (1R,2S,3R)-1-(2-(isoxazol-3-yl)-1H-imidazol-4-yl)butane-1,2,3,4-tetraol from a single crystal structure of the compound. Anisotropic atomic displacement ellipsoids for the non-hydrogen atoms are shown at the 50 percent probability level. Hydrogen atoms are displayed with an arbitrarily small radius.

5. DETAILED DESCRIPTION OF THE INVENTION

This invention is directed, in part, to solid (e.g., crystalline) forms of (1R,2S,3R)-1-(2-(isoxazol-3-yl)-1H-imidazol-4-yl)butane-1,2,3,4-tetraol and hydrates thereof. The compound is an inhibitor of SIP lyase, and is believed to be useful in the treatment of diseases and disorders such as multiple sclerosis and rheumatoid arthritis. See U.S. patent application Ser. No. 12/038,872 to Augeri et al., filed Feb. 28, 2008.

This invention is also directed to dosage forms comprising solid forms of (1R,2S,3R)-1-(2-(isoxazol-3-yl)-1H-imidazol-4-yl)butane-1,2,3,4-tetraol and hydrates thereof, and to methods of their use.

5.1. Definitions

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise indicated, a "prophylactically effective amount" of a compound is an amount sufficient to prevent a disease or condition, or one or more symptoms associated with the disease or condition, or to prevent its recurrence. A prophylactically effective amount of a compound means an amount of therapeutic agent, alone or in combination with other agents, which provides a prophylactic benefit in the prevention of the disease or condition. The term "prophylactically effective amount" can encompass an amount that improves overall prophylaxis or enhances the prophylactic efficacy of another prophylactic agent.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder or one or more of its symptoms, or retards or slows the progression of the disease or disorder.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should also be noted that any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit. Structures that represent compounds with one or more chiral centers, but which do not indicate stereochemistry (e.g., with bolded or dashed lines), encompasses pure stereoisomers and mixtures (e.g., racemic mixtures) thereof. Similarly, names of compounds having one or more chiral centers that do not specify the stereochemistry of those centers encompass pure stereoisomers and mixtures thereof.

5.2. Solid Forms

This invention is directed to solid forms of (1R,2S,3R)-1-(2-(isoxazol-3-yl)-1H-imidazol-4-yl)butane-1,2,3,4-tetraol:

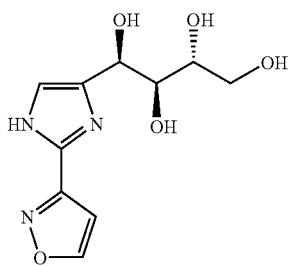

and hydrates thereof. Particular solid forms are crystalline.

One embodiment of the invention encompasses crystalline hydrates of (1R,2S,3R)-1-(2-(isoxazol-3-yl)-1H-imidazol-4-yl)butane-1,2,3,4-tetraol. A particular hydrate has a water: compound ratio of about 0.7 (i.e., about 0.7 mol water to 1.0 mol compound). In this context, the term "about" means±0.2 mol water.

Figure 1:
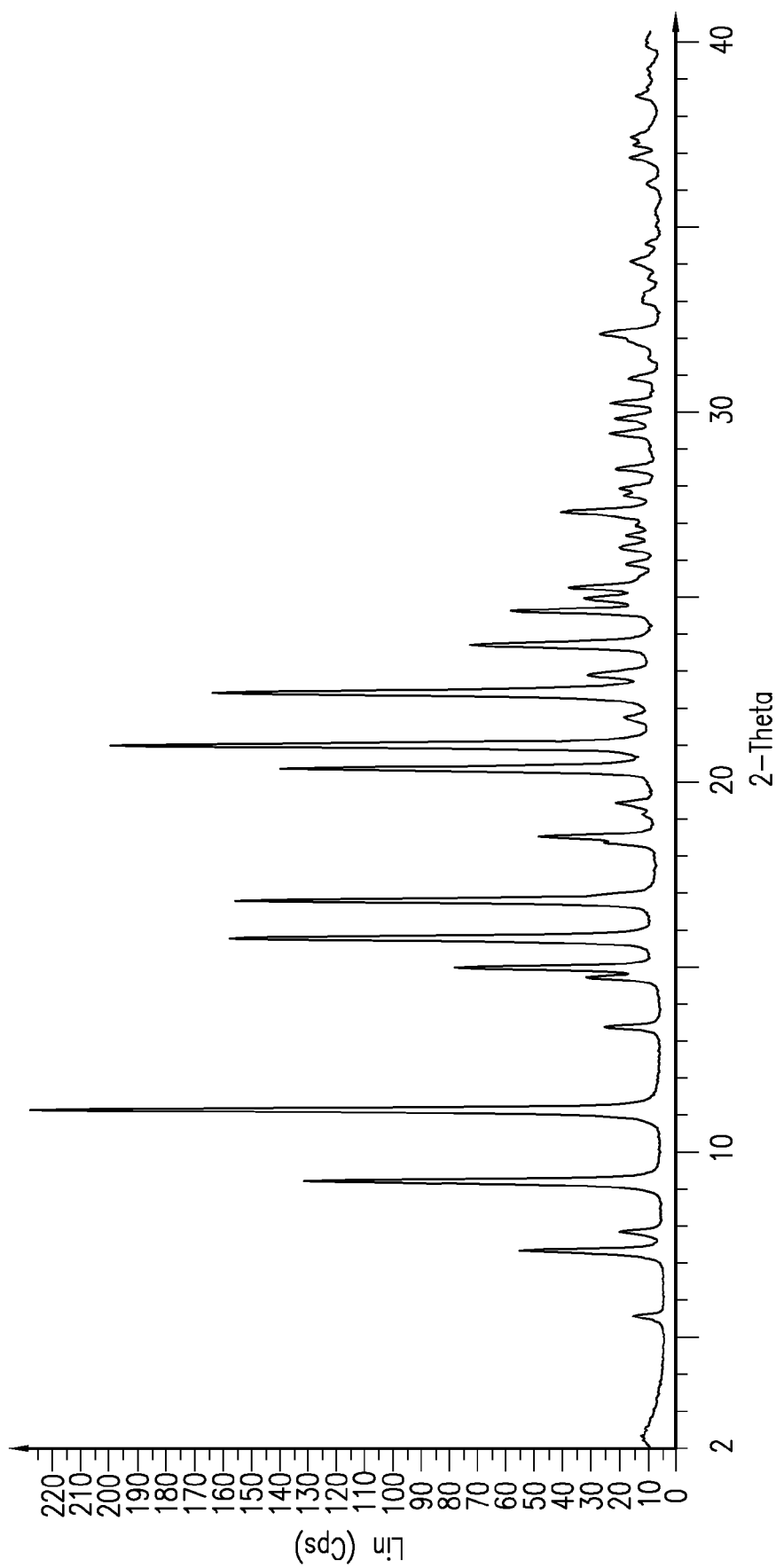
FIG. 1 is a X-ray powder diffraction (XRPD) pattern of crystalline (1R,2S,3R)-1-(2-(isoxazol-3-yl)-1H-imidazol-4-yl)butane-1,2,3,4-tetraol hydrate. The diffractogram was obtained using a Bruker D8 Advance System (Cu Kα radiation) with a VANTEC-1 detector.
Figure 2:
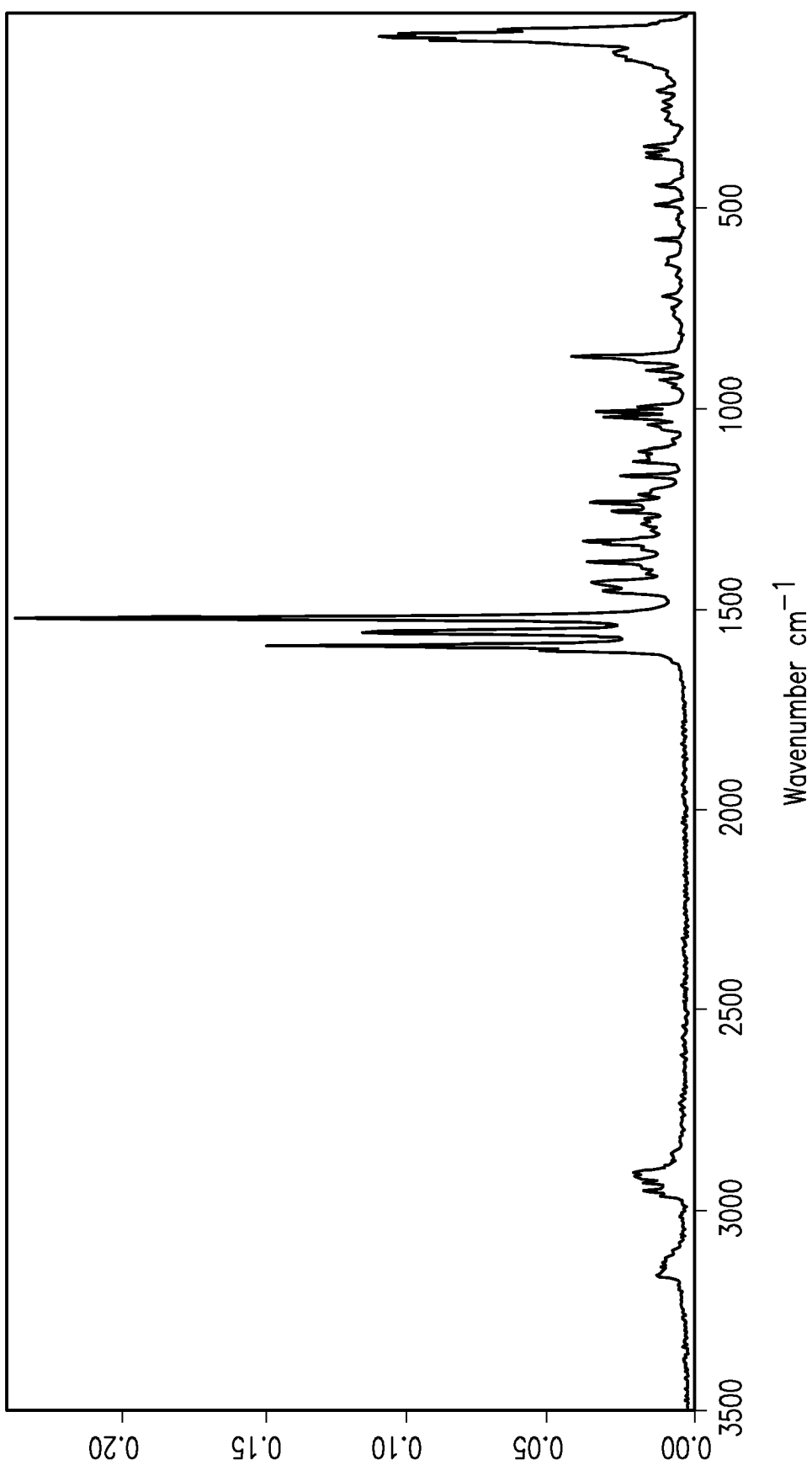
FIG. 2 is a FT-Raman spectrum of crystalline (1R,2S,3R)-1-(2-(isoxazol-3-yl)-1H-imidazol-4-yl)butane-1,2,3,4-tetraol hydrate. The spectrum was obtained using a Bruker RFS100 with 1064 nm excitation.

A particular hydrate has a differential scanning calorimetry (DSC) endotherm with a peak at about 164° C. In this context, the term "about" means±5.0° C. In one embodiment, the hydrate provides a X-ray powder diffraction (XRPD) pattern that contains peaks at about 9.2, 11.2, 15.8, 16.8, 20.4, 21.0 and/or 22.5 degrees 2θ. In this context, the term "about" means±0.3 degrees. As those skilled in the art are well aware, the relative intensities of peaks in a XRPD pattern can vary depending on how the sample is prepared and how the data is collected. With this in mind, an example of a XRPD pattern of this form is provided in FIG. 1. An example of a FT-Raman spectrum of this form is provided in FIG. 2.

Figure 3:
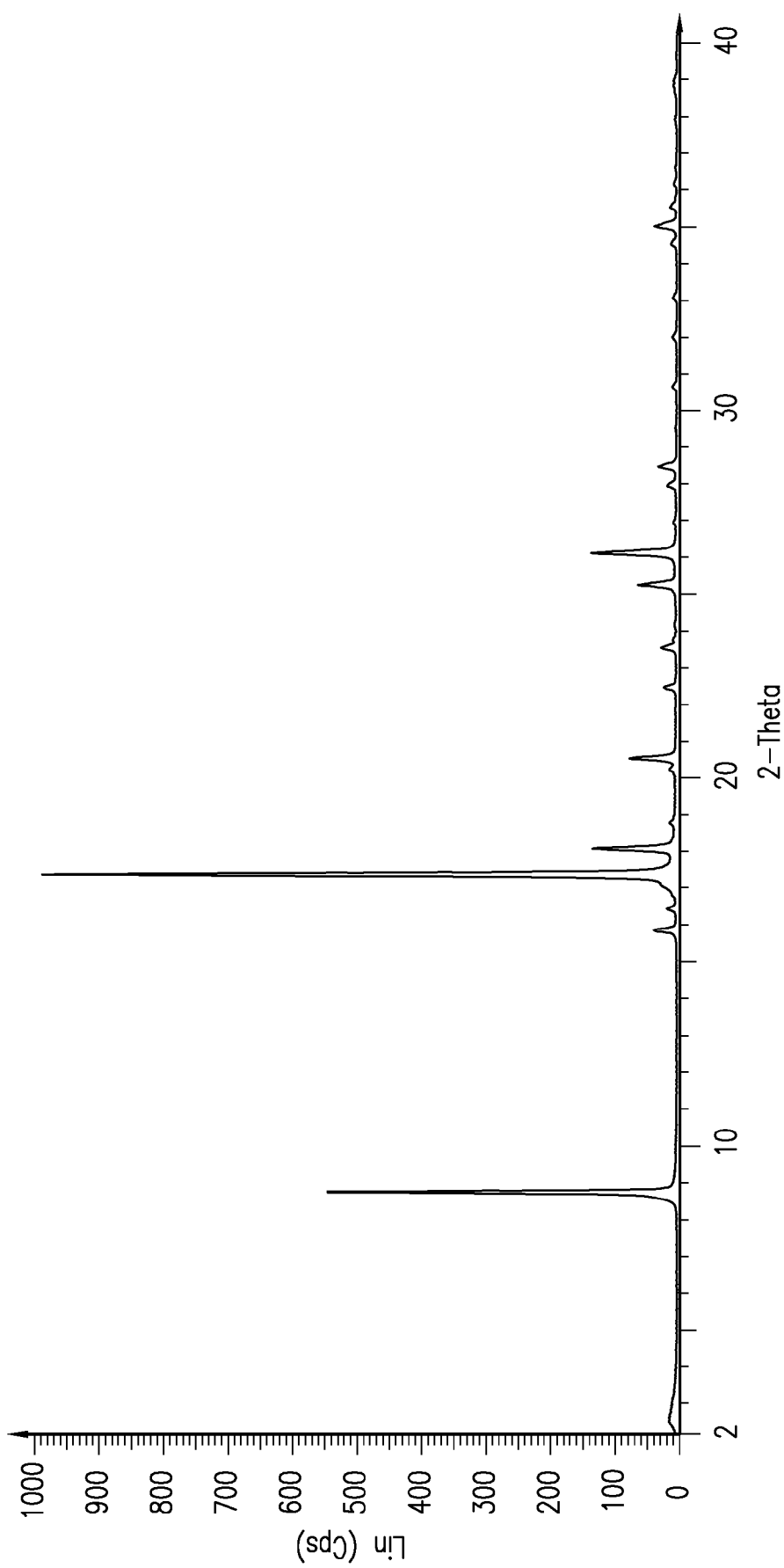
FIG. 3 is a XRPD pattern of crystalline anhydrous (1R,2S,3R)-1-(2-(isoxazol-3-yl)-1H-imidazol-4-yl)butane-1,2,3,4-tetraol. The diffractogram was obtained using a Bruker D8 Advance System (Cu Kα radiation) with a VANTEC-1 detector.
Figure 4:
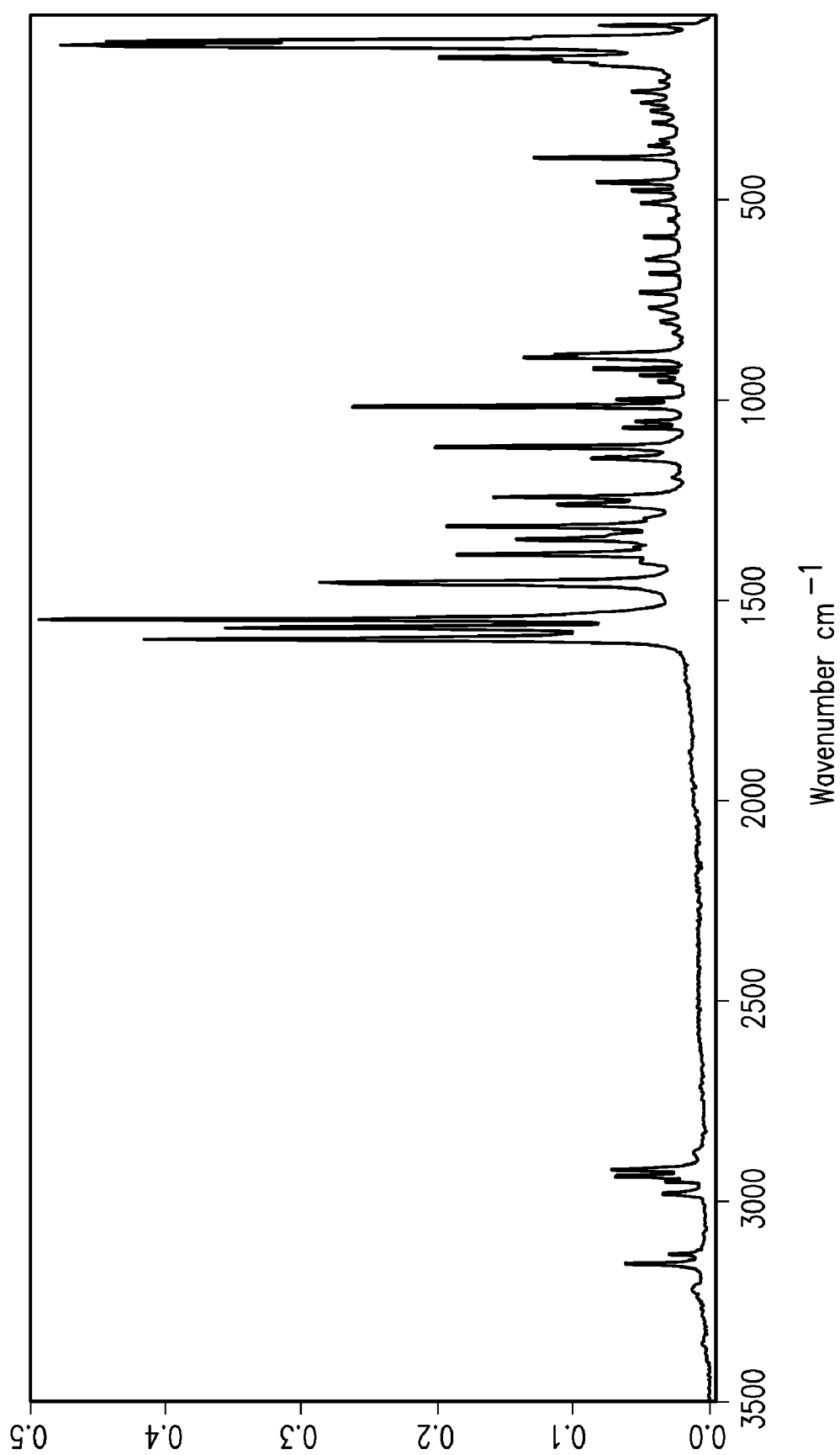
FIG. 4 is a FT-Raman spectrum of crystalline anhydrous (1R,2S,3R)-1-(2-(isoxazol-3-yl)-1H-imidazol-4-yl)butane-1,2,3,4-tetraol. The spectrum was obtained using a Bruker RFS100 with 1064 nm excitation.

Another embodiment encompasses crystalline anhydrous (1R,2S,3R)-1-(2-(isoxazol-3-yl)-1H-imidazol-4-yl)butane-1,2,3,4-tetraol. One form of this compound has a DSC endotherm with a peak at about 204° C. In this context, the term "about" means±5.0° C. This form provides a XRPD pattern that contains peaks at about 8.6, 17.3, 18.0, 25.2 and/or 26.1 degrees 2θ. In this context, the term "about" means±0.2 degrees. An example of a XRPD pattern of this form is provided in FIG. 3. An example of a FT-Raman spectrum of this form is provided in FIG. 4.

Solid forms of (1R,2S,3R)-1-(2-(isoxazol-3-yl)-1H-imidazol-4-yl)butane-1,2,3,4-tetraol can be obtained as single crystals, and single crystals of sufficient quality may be used to obtain single crystal X-ray structures of the compound. For example, a single crystal of anhydrous (1R,2S,3R)-1-(2-(isoxazol-3-yl)-1H-imidazol-4-yl)butane-1,2,3,4-tetraol was used to generate the three-dimensional structure shown in FIG. 5.

This invention encompasses solids that are mixtures of both amorphous and crystalline forms. Certain solids comprise crystalline (1R,2S,3R)-1-(2-(isoxazol-3-yl)-1H-imidazol-4-yl)butane-1,2,3,4-tetraol or a pharmaceutically acceptable hydrate thereof in an amount of at least about 50, 75, 80, 85, 90, 95 or 99 weight percent.

5.3. Methods of Use

This invention encompasses a method of modulating (e.g., increasing) the amount of S1P in a patient (e.g., a human) in need thereof, which comprises administering to the patient an effective amount of a compound of the invention (i.e., a compound disclosed herein).

Another embodiment encompasses a method of reducing the number of T-cells in the blood of a patient, which comprises administering to the patient an effective amount of a compound of the invention.

Another embodiment encompasses a method of treating, managing or preventing a disease affected by (or having symptoms affected by) S1P levels, which comprises administering to a patient in need thereof a therapeutically or prophylactically effective amount of a compound of the invention.

Another embodiment encompasses a method of suppressing immune response in a patient, which comprises administering to the patient an effective amount of a compound of the invention.

Another embodiment encompasses a method of treating, managing or preventing an autoimmune or inflammatory disease or disorder, which comprises administering to a patient in need thereof a therapeutically or prophylactically effective amount of a compound of the invention. Examples of diseases and disorders include ankylosing spondylitis, asthma (e.g., bronchial asthma), atopic dermatitis, Behcet's disease, graft-vs-host disease, Kawasaki syndrome, lupus erythematosus, multiple sclerosis, myasthenia gravis, pollinosis, psoriasis, psoriatic arthritis, rheumatoid arthritis, scleroderma, transplant rejection (e.g., of organ, cell or bone marrow), type 1 diabetes, and uveitis.

Additional diseases and disorders include Addison's Disease, anti-phospholipid syndrome, autoimmune atrophic gastritis, achlorhydra autoimmune, Celiac Disease, Crohn's Disease, Cushing's Syndrome, dermatomyositis, Goodpasture's Syndrome, Grave's Disease, Hashimoto's thyroiditis, idiopathic adrenal atrophy, idiopathic thrombocytopenia, Lambert-Eaton Syndrome, pemphigoid, pemphigus vulgaris, pernicious anemia, polyarteritis nodosa, primary biliary cirrhosis, primary sclerosing cholangitis, Raynauds, Reiter's Syndrome, relapsing polychondritis, Schmidt's Syndrome, Sjogren's Syndrome, sympathetic ophthalmia, Takayasu's Arteritis, temporal arteritis, thyrotoxicosis, ulcerative colitis, and Wegener's granulomatosis.

The amount, route of administration and dosing schedule of a compound will depend upon factors such as the specific indication to be treated, prevented, or managed, and the age, sex and condition of the patient. The roles played by such factors are well known in the art, and may be accommodated by routine experimentation. In a particular embodiment, a compound of the invention is administered to a human patient in an amount of from about 0.5 to about 5 mpk.

5.4. Pharmaceutical Formulations

This invention encompasses pharmaceutical compositions comprising one or more compounds of the invention. Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds of this invention from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

The composition, shape, and type of a dosage form will vary depending on its use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

5.4.1. Oral Dosage Forms

Pharmaceutical compositions of the invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See, e.g., *Remington's Pharmaceutical Sciences,* 18th ed., Mack Publishing, Easton Pa. (1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

5.4.2. Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are specifically sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5.4.3. Transdermal, Topical and Mucosal Dosage Forms

Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers may be used to assist in delivering active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates may also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or hydrates of the active ingredients can be used to further adjust the properties of the resulting composition.

6. EXAMPLES

Aspects of this invention can be understood from the following examples.

6.1. Preparation of (1Z,2E)-N-hydroxy-2-(hydroxyimino)-acetimidoyl chloride

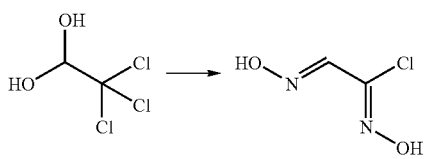

To a dried 50 L three-necked flask equipped with a thermometer controller, a mechanical stirrer, and a dropping funnel protected under nitrogen was charged 6060 g (2.4×) of water and 3151 g (1.26×) of hydroxylamine hydrochloride. The reaction mixture was stirred at 20-25° C. for 10-30 minutes until the solids was dissolved. To the solution was added drop wise a clear solution of 3134 g (1.25×) of potassium carbonate and 28000 g (11.2×) of water over 30-50 minutes at 20-25° C. followed by 2500 g (1.0×) of chloral hydrate in portions at 20-28° C. After addition, the reaction mixture was stirred at 25-30° C. for 4-5 hours and deemed complete by HPLC. The reaction mixture was cooled to 0-5° C. followed by addition of 9673 g (3.87×) of 25% sodium hydroxide for 60-90 minutes at 0-5° C. After addition, the stirring mixture was acidified with 12200 g (4.89×) of 25% sulfuric acid at 0-5° C. until pH=3.0-3.5. The resulting mixture was extracted twice with 2775 g (1.11×) of methyl t-butyl ether. The combined organic layer was dried with 1000 g (0.4×) of sodium sulfate, filtered and then concentrated under low pressure to 1500 g (0.6×) volume, which was diluted by 2670 g (1.08×) of n-heptane and concentrated again to 1500 g (0.6×) volume. The resulting slurry was added 2670 g (1.08×) of n-heptane, and then cooled to 0-5° C. and kept at this temperature for 1 hour. After filtration, the wet cake was washed twice with 250 g (0.1×) of n-heptane. The wet cake was dried under vacuum for 48 hrs at 30-38° C. to yield 737.0 g of off-white solid (Assay 98.3%, purity: 99.2%, yield 40%). $^1$H NMR (DMSO-$d_6$, 400 MHz) δ 12.44 (s, 1H), 12.23 (s, 1H), 8.27 (s, 1H); $^{13}$C NMR (DMSO-$d_6$, 100 MHz) δ 143.19, 137.83; Elemental analysis: Found: C, 19.54; N, 22.30; H, 2.64. Calculated for $C_2H_3N_2O_2Cl$: C, 19.61; N, 22.87; H, 2.47.

6.2. Preparation of 5-ethoxy-4,5-dihydroisoxazole-3-carbonitrile

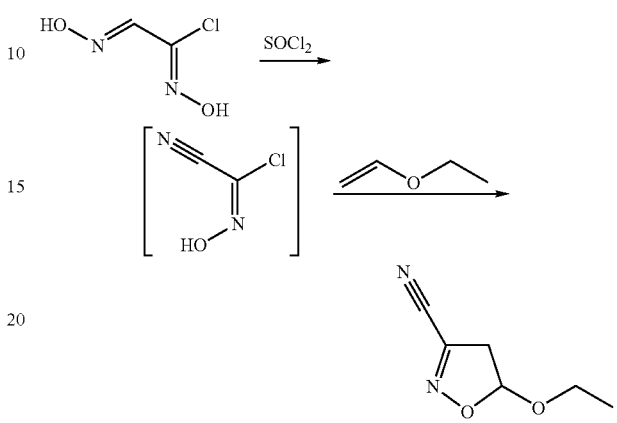

To a dried 10 L three-necked flask equipped with a thermometer controller, a mechanical stirrer, and a dropping funnel protected under nitrogen was charged 6966.7 g (7.3×) of tetrahydrofuran and 950.0 g (1.0×) of compound (1Z,2E)-N-hydroxy-2-(hydroxyimino)acetimidoyl chloride. The reaction mixture was cooled to 0-5° C. followed by drop wise addition of 1845.2 g (1.9×) thionyl chloride over 60-90 minutes at 0-5° C. After addition, the reaction mixture was stirred at 10-15° C. for 6-7 hours and deemed complete by HPLC. The reaction mixture was then concentrated under vacuum at 15-20° C. to about 1.0 L (1.0×) followed by addition of a total of 950 g (0.9×) of tetrahydrofuran and distillation to remove residual thionyl chloride. The resulting mixture was added drop wise into a solution of 2755 g (2.9×) of ethoxyethene, 6764 g (7.12×) of tetrahydrofuran and 715.0 g (0.75×) of sodium carbonate in 3200.0 g (3.4×) of water over 30-40 minutes at 0-5° C. After addition, the reaction mixture was stirred at 0-5° C. for 1-2 hours and deemed complete by HPLC. The resulting mixture was separated and the aqueous layer was extracted with 1900 g (2.0×) of methyl t-butyl ether, and then the combined organic layer was dried with 380 g (0.4×) of sodium sulfate, filtered and then concentrated to give 549.7 g yellow oil (Assay 60.3%, purity 97.0%, yield 30.5%). $^1$H NMR (CDCl$_3$, 400 MHz) δ 5.76 (dd, J=2.0 Hz, 4.8 Hz, 1H), 3.86-3.90 (m, 1H), 3.60-3.65 (m, 1H), 3.21 (dd, J=6.8 Hz, 11.2 Hz, 1H), 3.00 (dd, J=2.0 Hz, 16 Hz, 1H), 1.21 (T, J=6.8 Hz, 1H).

6.3. Preparation of isoxazole-3-carbonitrile

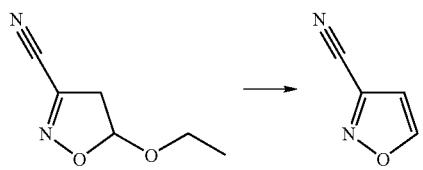

To a dried 10 L three-necked flask equipped with a thermometer controller, a mechanical stirrer, and a dropping funnel protected under nitrogen was charged 52000 g (18.6×) of dichloromethane and 289.8 g (1.0×, 449.3 g assayed at 64.5 wt %, 289.8 g real) of 5-ethoxy-4,5-dihydroisoxazole-3-carbonitrile. The reaction mixture was cooled to 0-5° C. followed by drop wise addition of 173.8 g (0.6×) of diazabicyclo [5.4.0]undecene for 20-30 minutes at 0-5° C. After addition, the reaction mixture was stirred at 0-5° C. for 2-3 hours and deemed complete by HPLC. The stirring mixture was neutralized with 1000.0 g (3.45×) of 0.1N hydrogen chloride at 0-5° C. to pH 6.5-7.0. The resulting mixture was extracted twice with 1170 g (4.0×) of methyl t-butyl ether. After separation, the combined organic layer was dried with 116 g (0.4×) of sodium sulfate, filtered and then concentrated under vacuum to give the crude isoxazole-3-carbonitrile (544.6 g assayed 21.99 wt %, 119.8 g real, 62% yield). Subsequent distillation (40° C./5 mmHg) gave 97.3 g of colorless oil (Purity 99%, yield 50%). $^1$H NMR (CDCl$_3$, 400 MHz) δ 8.64 (d, J=1.6 Hz, 1H), 6.70 (d, J=1.6 Hz, 1H); $^{13}$C NMR (CDCl$_3$, 100 MHz) δ 160.92, 139.19, 109.95, 107.40; Elemental analysis: Found: C, 50.02; N, 27.74, H 2.18. Calculated for C$_4$H$_2$N$_2$O: C, 51.07; N, 29.78; 2.14.

6.4. Preparation of (1R,2S,3R)-1-(2-(isoxazol-3-yl)-1H-imidazol-4-yl)butane-1,2,3,4-tetraol

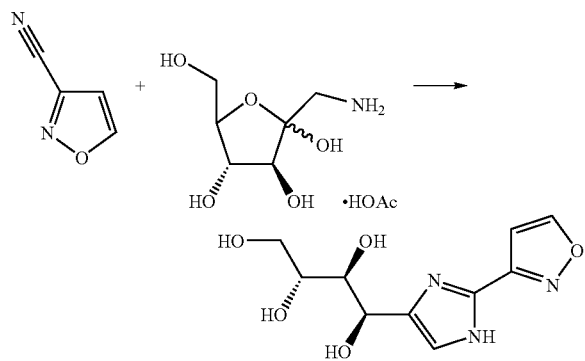

To a dried 10 L three-necked flask equipped with a thermometer controller, a mechanical stirrer, and a dropping funnel protected under nitrogen was charged 336.2 g (1.0×) of isoxazole-3-carbonitrile and 4125.0 g (12.3×) of methanol. To the stirring solution was added 449.2 g (1.34×) of sodium methoxide in methanol (25-30 wt %) over 15 min. The mixture was stirred at 20-25° C. overnight. The above solution was transferred into a slurry of 880.68 g (2.62×) of fructosamine acetic acid salt in 4125 g (12.3×) of methanol over 15 minutes and the mixture was stirred at 20-25° C. for 6 h. Another 400.0 g (1.2×) of sodium methoxide in methanol (25-30 wt %) was then added to the mixture over 10 minutes and the mixture was stirred for additional 6 h and deemed complete by HPLC. The reaction mixture was then diluted with 3362.3 g (10.0×) of water and concentrated under pressure to remove methanol, filtered and the cake was washed twice with 243.2 g (0.7×) of water to yield 1140 g of off-white solid (Purity 99.0%, assay 60%).

6.5. Crystallization of (1R,2S,3R)-1-(2-(isoxazol-3-yl)-1H-imidazol-4-yl)butane-1,2,3,4-tetraol hydrate Five grams of the di-HCl salt of (1R,2S,3R)-1-(2-(isoxazol-3-yl)-1H-imidazol-4-yl)butane-1,2,3,4-tetraol were dissolved in 50 mL water to provide a clear solution. To this solution was added 1M NaOH until the pH reached about 10 and solids precipitated. The solids were filtered and collected to obtain 5.6 g of (1R,2S,3R)-1-(2-(isoxazol-3-yl)-1H-imidazol-4-yl)butane-1,2,3,4-tetraol free base wet cake.

To the wet cake from above was added 50 mL of water (10×), and the resulting mixture was heated to 99-100° C. to provide a clear tan solution. Upon cooling, solids began to crystallize out of solution. Further cooling caused more solids to crystallize until the stirring became problematic. At this point the solids were filtered, collected (2.36 g of free base) and dried under vacuum overnight at 50° C. Upon further cooling the filtrate produced a second crop of crystals.

6.6. Alternate Crystallization of (1R,2S,3R)-1-(2-(isoxazol-3-yl)-1H-imidazol-4-yl)butane-1,2,3,4-tetraol hydrate To a dried 20 L three-necked flask equipped with a thermometer controller, a mechanical stirrer, and a dropping funnel protected under nitrogen was charged 1200 g (1R,2S,3R)-1-(2-(isoxazol-3-yl)-1H-imidazol-4-yl)butane-1,2,3,4-tetraol and 14000.0 g (11.7×) of water. The mixture was heated to 90-97° C. until the solid was dissolved completely. After polish filtration, the solution was cooled to 15-20° C., filtered, washed with 1200 g (1.0×) of water and 1200 g (1.0×) of ethanol, then dried under vacuum at 40-45° C. to yield 980 g of captioned compound as a white solid.

6.7. Crystallization of Anhydrous (1R,2S,3R)-1-(2-(isoxazol-3-yl)-1H-imidazol-4-yl)butane-1,2,3,4-tetraol (1R,2S,3R)-1-(2-(isoxazol-3-yl)-1H-imidazol-4-yl)butane-1,2,3,4-tetraol hydrate (726 g) was heated in 7200.0 g (10.0×) of ethanol for 3-3.5 h at 75-80° C., and then cooled slowly to 10-15° C. and stirred for 2-2.5 h at 10-15° C. The solids were filtered, washed with 726 g (1.0×) of ethanol and dried under vacuum for 20 hrs at 30-40° C. to yield 663 g of anhydrous (1R,2S,3R)-1-(2-(isoxazol-3-yl)-1H-imidazol-4-yl)butane-1,2,3,4-tetraol as off-white solid. $^1$H NMR (DMSO-d$_6$ with a drop of DCl, 400 MHz) δ 8.71 (t, J=0.8 Hz, 1H), 7.40 (s, 1H), 6.89 (t, J=0.8 Hz, 1H), 5.06 (d, J=1.2 Hz, 1H), 3.53-3.69 (m, 3H), 3.49-3.52 (m, 1H); $^{13}$C NMR (DMSO-d$_6$ with a drop of DCl, 100 MHz) δ 163.2, 149.6, 139.0, 133.0, 118.5, 104.8, 73.4, 71.4, 65.2, 63.8; Elemental analysis: Found: C, 44.50; N, 15.77; H, 5.39. Calculated for C$_{10}$H$_{13}$N$_3$O$_5$: C, 47.06; N, 16.46; H, 5.13.

6.8. Single Crystal Structure of Anhydrous (1R,2S,3R)-1-(2-(isoxazol-3-yl)-11H-imidazol-4-yl)butane-1,2,3,4-tetraol Crystals of (1R,2S,3R)-1-(2-(isoxazol-3-yl)-1H-imidazol-4-yl)butane-1,2,3,4-tetraol were grown from nitromethane by slow evaporation after maturation for 48 hours. Crystals having two types of morphology were observed: very fine needles and rods. A rod shaped crystal was used to obtain a single crystal structure of the compound.

Data was obtained using a Pt-135 Apex CCD area detector, Microstar H Rotating Cu Anode (Cu Kα), and Bruker SHELXTL software. The refinement technique was full-matrix least-squares on F$^2$. The goodness of fit on F$^2$ was 1.004. The single crystal form exhibited the properties listed in Table 1, below.

TABLE 1

| Sample and Crystal Data | |
|---|---|
| Crystal habit | Colorless lath |
| Crystal system | Monoclinic |
| Space group | P2$_1$ |
| Unit cell dimensions | a = 4.8401(3) Å    α = 90° |
| | b = 20.2537(13) Å    β = 92.042(2)° |
| | c = 5.5882(4) Å    γ = 90° |
| Volume | 547.46(6) Å$^3$ |
| Z | 2 |
| Density (calculated) | 1.548 Mg/m$^3$ |

FIG. 5 provides a view of a molecule of the compound from the crystal structure.

All references (e.g., patents and patent applications) cited above are incorporated herein by reference in their entireties.

What is claimed is:

1. A crystalline hydrate of (1R,2S,3R)-1-(2-(isoxazol-3-yl)-1H-imidazol-4-yl)butane-1,2,3,4-tetraol.

2. A crystalline anhydrite of (1R,2S,3R)-1-(2-(isoxazol-3-yl)-1H-imidazol-4-yl)butane-1,2,3,4-tetraol.

3. A pharmaceutical composition comprising the crystalline hydrate of claim 1.

4. A pharmaceutical composition comprising the crystalline anhydrate of claim 2.

5. A method of reducing the number of circulating lymphocytes in a patient, which comprises administering to the patient an effective amount of the crystalline hydrate of claim 1.

6. A method of reducing the number of circulating lymphocytes in a patient, which comprises administering to the patient an effective amount of the crystalline anhydrate of claim 2.

7. A method of treating or managing rheumatoid arthritis, which comprises administering to a patient in need thereof a therapeutically effective amount of the crystalline hydrate of claim 1.

8. A method of treating or managing rheumatoid arthritis, which comprises administering to a patient in need thereof a therapeutically effective amount of the crystalline anhydrate of claim 2.

* * * * *